(12) United States Patent
Schelberger et al.

(10) Patent No.: US 6,258,801 B1
(45) Date of Patent: Jul. 10, 2001

(54) FUNGICIDAL MIXTURES

(75) Inventors: Klaus Schelberger, Gönnheim; Maria Scherer, Landau; Reinhold Saur, Böhl-Iggelheim; Hubert Sauter, Mannheim; Bernd Müller, Frankenthal; Erich Birner, Altleiningen; Joachim Leyendecker, Ladenburg; Eberhard Ammermann, Heppenheim; Gisela Lorenz, Neustadt; Siegfried Strathmann, Limburgerhof, all of (DE)

(73) Assignee: BASF Aktiengesellshcaft, Ludwigshafen (DE)

( * ) Notice: Subject to any disclaimer, the term of this patent is extended or adjusted under 35 U.S.C. 154(b) by 0 days.

(21) Appl. No.: 09/423,462

(22) PCT Filed: May 15, 1998

(86) PCT No.: PCT/EP98/02877

§ 371 Date: Nov. 9, 1999

§ 102(e) Date: Nov. 9, 1999

(87) PCT Pub. No.: WO98/53691

PCT Pub. Date: Dec. 3, 1998

(30) Foreign Application Priority Data

May 28, 1997 (DE) .............................. 197 22 225

(51) Int. Cl.$^7$ .......................... A01N 57/18; A01N 43/64; A01N 43/56; A01N 57/00
(52) U.S. Cl. ..................... 514/141; 514/89; 514/91; 514/95; 514/99; 514/383; 514/407
(58) Field of Search ..................... 514/141, 89, 91, 514/95, 99, 383, 407

(56) References Cited

FOREIGN PATENT DOCUMENTS

| 2224890 | 2/1997 | (CA) . |
| 24 63 046 | 6/1975 | (DE) . |
| 741 970 | 11/1996 | (EP) . |
| 1449394 | 9/1976 | (GB) . |
| 96/01256 | 1/1996 | (WO) . |
| 96/01258 | 1/1996 | (WO) . |
| 96/03047 | 2/1996 | (WO) . |

Primary Examiner—Allen J. Robinson
(74) Attorney, Agent, or Firm—Keil & Weinkauf

(57) ABSTRACT

A fungicidal mixture, comprising
a) a carbamate of the formula I,

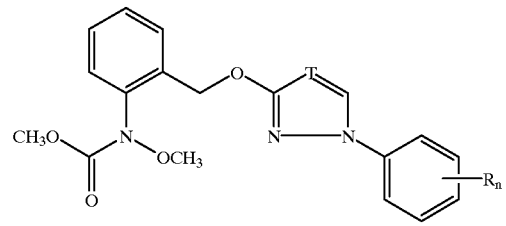

I where T is CH or N, n is 0, 1 or 2 and R is halogen, $C_1$–$C_4$-alkyl or $C_1$–$C_4$-haloalkyl, and where the radicals R may be different if n is 2, and
b) an active compund of the formula II,

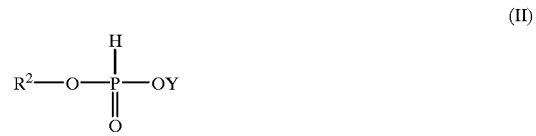

(II)

where:
Y is hydrogen, a metal atom of the 1st to 3rd main group of the Periodic Table of the Elements or a group $NR^3R^4R^5R^6$;
$R^2$ is hydrogen, a $C_1$–$C_{18}$-alkyl group which may be substituted by halogen or a nitro group, a $C_2$–$C_8$-alkenyl or $C_2$–$C_8$-alkinyl group which may be substituted by halogen or a nitro group, a $C_1$–$C_8$-alkoxy-$C_1$–$C_8$-alkyl or a $C_2$–$C_8$-alkenyl-$C_1$–$C_8$-alkyl group, an unsubstituted or substituted aryl group having 6 to 14 carbons, a $C_3$–$C_7$-cycloalkyl group, a $C_1$–$C_4$-alkylaryl group or a heterocyclic group having 5 or 6 ring atoms and a hetero atom from the group consisting of N, O and S, where the heterocyclic group is attached directly or via an aliphatic chain to the oxygen atom, and
$R^3$–$R^6$ independently of one another are each a $C_1$–$C_4$-alkyl group or a $C_1$–$C_4$-hydroxyalkyl group
in a synergistically effective amount,
is described.

8 Claims, No Drawings

FUNGICIDAL MIXTURES

This application is a 371 of PCT/EP98/02877, filed May 15, 1998.

The present invention relates to fungicidal mixtures which comprise a) a carbamate of the formula I,

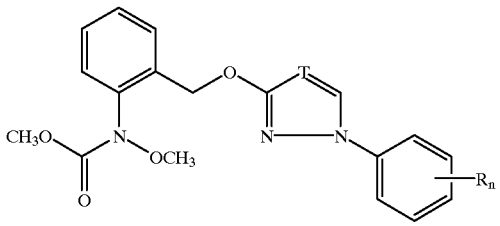

where T is CH or N, n is 0, 1 or 2 and R is halogen, $C_1$–$C_4$-alkyl or $C_1$–$C_4$-haloalkyl, and where the radicals R may be different if n is 2, and b) an active compound of the formula II,

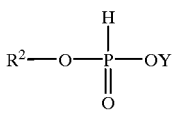

where:

Y is hydrogen, a metal atom of the 1st to 3rd main group of the Periodic Table of the Elements or a group $NR^3R^4R^5R^6$;

$R^2$ is hydrogen, a $C_1$–$C_{18}$-alkyl group which may be substituted by halogen or a nitro group, a $C_2$–$C_8$-alkenyl or $C_2$–$C_8$-alkinyl group which may be substituted by halogen or a nitro group, a $C_1$–$C_8$-alkoxy-$C_1$–$C_8$-alkyl or a $C_2$–$C_8$-alkenyl-$C_1$–$C_8$-alkyl group, an unsubstituted or substituted aryl group having 6 to 14 carbons, a $C_3$–$C_7$-cycloalkyl group, a $C_1$–$C_4$-alkylaryl group or a heterocyclic group having 5 or 6 ring atoms and a hetero atom from the group consisting of N, O and S, where the heterocyclic group is attached directly or via an aliphatic chain to the oxygen atom, and $R^3$–$R^6$ independently of one another are each a $C_1$–$C_4$-alkyl group or a $C_1$–$C_4$-hydroxyalkyl group in a synergistically effective amount.

Moreover, the invention relates to methods for controlling harmful fungi using mixtures of the compounds I and II and to the use of the compounds I and II for preparing such mixtures.

The compounds of the formula I, their preparation and their action against harmful fungi are disclosed in the literature (WO-A 96/01,256 and 96/01,258).

In the literature, the compounds II are described as fungicides and insecticides (for example DE 24 63 046 and literature cited therein). A known representative of this class of active compounds is commercially available under the common name fosetyl or fosetyl-Al.

Processes for preparing the compounds of the formula II are known per se to the person skilled in the art and therefore do not require any further mention here.

It is an object of the present invention to provide mixtures which have an improved activity against harmful fungi combined with a reduced total amount of active ingredients applied (synergistic mixtures), with a view to reducing the application rates and improving the activity spectrum of the known compounds.

We have found that this object is achieved by the mixtures defined at the outset. Moreover, we have found that applying the compounds I and II simultaneously, i.e. together or separately, or applying the compounds I and II in succession provides better control of harmful fungi than is possible with the individual compounds alone.

The formula I represents, in particular, carbamates in which the combination of the substituents corresponds to one row of the table below:

TABLE 1

| No. | T | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl, 4-$CH_3$ |
| I.52 | CH | 3-Cl, 4-$CH_3$ |

Particular preference is given to the compounds I.12, I.23, I.32 and I.38.

The formula II represents in particular compounds in which $R^2$ is hydrogen or a $C_1$–$C_4$-alkyl group and in particular an ethyl group (—$CH_2CH_3$) and Y is a metal of the 3rd group of the Periodic Table of the Elements. Suitable metals are also metals of the first and the second main group such as Li, K, Na, Cs, Mg or Ca, to give just some examples.

However, in principle compounds II are suitable in which $R^2$ and $R^3$–$R^6$ are as defined at the outset.

A particularly preferred compound II is the active compound known under the name fosetyl, or its Al salt fosetyl-Al.

In relation to the C=Y or C=CH or C=N double bonds, the compounds of the formula I can be present in the E or Z configuration (in relation to the carboxylic acid function). Accordingly, they can be used in the mixture according to the invention in each case either as pure E or Z isomers or as E/Z isomer mixture. The E/Z isomer mixture or the Z isomer is preferably used, the Z isomer being especially preferred.

The C=N double bonds of the oxime ether groups in the side chain of the compounds I can exist in each case in the form of pure E or Z isomers or in the form of E/Z isomer mixtures. The compounds I can be used in the mixtures according to the invention both as isomer mixtures and as pure isomers. With a view to their use, particular preference is given to compounds I in which the terminal oxime ether grouping of the side chain is in the cis configuration ($OCH_3$ to ZR').

Owing to their basic character, the compounds I are capable of forming salts or adducts with inorganic or organic acids or with metal ions.

Examples of inorganic acids include hydrohalic acids such as hydrofluoric acid, hydrochloric acid, hydrobromic acid and hydroiodic acid, sulfuric acid, phosphoric acid and nitric acid.

Suitable organic acids are, for example, formic acid, carboxylic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfo groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphoric acid radicals), it being possible for the alkyl or aryl radicals to carry further substituents, e.g. p-toluenesulfonic acid, salicylic acid, p-aminosalicylic acid, 2-phenoxybenzoic acid, 2-acetoxybenzoic acid, etc.

Suitable metal ions are, in particular, the ions of the elements of the second main group, in particular calcium and magnesium, of the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period. The metals can exist in the various valencies which they can assume.

When preparing the mixtures, it is preferred to employ the pure active ingredients I and II, to which further ingredients active against harmful fungi or other pests, such as insects, arachnids or nematodes, or herbicidal or growth-regulating active ingredients or fertilizers can be admixed, if so required.

The mixtures of the compounds I and II, or the simultaneous joint or separate use of the compounds I and II, have outstanding action against a wide spectrum of phytopathogenic fungi, in particular from the classes of the Ascomycetes, Deuteromycetes, Phycomycetes and Basidiomycetes. Some of them act systemically and can therefore also be employed as foliar- and soil-acting fungicides.

They are especially important for controlling a large number of fungi in a variety of crop plants, such as cotton, vegetable species (e.g. cucumbers, beans and cucurbits), barley, grass, oats, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cineres* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, Pseudoperonospora species in cucurbits and hops, *Plasmopara viticola* in grapevines, Alternaria species in vegetables and fruit, and Fusarium and Verticillium species.

Furthermore, they can be used in the protection of materials (e.g. in the protection of wood), for example against *Paecilomyces variotii*.

The compounds I and II can be applied simultaneously together or separately or in succession, the sequence, in the case of separate application, generally not having any effect on the result of the control measures.

The compounds I and II are usually used in a weight ratio of from 0.05:1 to 20:1, preferably from 0.1:1 to 10:1, in particular from 0.2:1 to 5:1 (II:I).

The application rates of the mixtures according to the invention are, in the case of the compounds I, from 0.005 to 0.5 kg/ha, preferably from 0.05 to 0.5 kg/ha, in particular from 0.05 to 0.2 kg/ha, depending on the nature of the desired effect.

Correspondingly, in the case of the compounds II, the application rates are generally from 0.01 to 2 kg/ha, preferably from 0.05 to 1 kg/ha, in particular from 0.1 to 0.8 kg/ha.

For seed treatment, the application rates of the mixture are generally from 0.001 to 100 g/kg of seed, preferably from 0.01 to 50 g/kg, in particular from 0.01 to 10 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in each case, it should ensure as fine and uniform as possible a distribution of the mixture according to the invention.

The formulations are prepared in a manner known per se, e.g. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or jointly grinding the compounds I and II, or the mixture of the compounds I and II, with a solid carrier.

Granules (e.g. coated granules, impregnated granules or homogeneous granules) are usually prepared by binding the active ingredient, or active ingredients, to a solid carrier.

Fillers or solid carriers are, for example, mineral earths, such as silica gel, silicas, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably from 0.5 to 90% by weight, of one of the compounds I or II, or of the mixture of the compounds I and II. The active ingredients are employed in a purity of from 90% to 100%, preferably from 95% to 100% (according to NMR spectrum or HPLC.

The compounds I or II, or the mixtures, or the corresponding formulations, are applied by treating the harmful fungi or the plants, seeds, soils, areas, materials or spaces to be kept free from them with a fungicidally effective amount of the mixture, or of the compounds I and II in the case of separate application. Application can be effected before or after infection by the harmful fungi.

USE EXAMPLE 1

Activity Against *Plasmopara viticola*

Leaves of potted grapevines cv. "Müller-Thurgau" were sprayed to runoff point with an aqueous preparation of active compound which had been prepared from a stock solution comprising 10% of active ingredient, 63% of cyclohexanone and 27% of emulsifier. To assess the persistency of the substances, the plants were kept for 7 days in a greenhouse after the spray coating had dried on. only then were the leaves inoculated with an aqueous zoospore suspension of Plasmopara viticola. The grapevines were then initially kept in a water vapor-saturated chamber at 24° C. for 48 hours and then in a greenhouse at 20–24° C. for 5 days and subsequently in a greenhouse at 20–30° C. for 5 days. After this period of time, the plants were once more kept in a humid chamber for 16 hours to promote sporangiophore eruption. The extent of the infection on the undersides of the leaves was then assessed visually.

Evaluation is carried out by determining the infected leaf areas in percent. These percentages are converted into efficacies. The expected efficacies of the mixtures of the active ingredients are determined using Colby's formula [R. S. Colby, Weeds 15, 20–22 (1967)] and compared with the observed efficacies.

Colby's formula:

$$E = x + y + z - x \cdot y \cdot z / 100$$

E expected efficacy, expressed in % of the untreated control, when using the mixture of the active ingredients A, B and C at the concentrations a, b and c x efficacy, expressed in % of the untreated control, when using active ingredient A at a concentration of a y efficacy, expressed in % of the untreated control, when using active ingredient B at a concentration of b z efficacy, expressed in % of the untreated control, when using active ingredient C at a concentration of c The efficacy (E) is calculated as follows using Abbot's formula:

$$E = (1 - \alpha) \cdot 100 / \beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants are not infected.

TABLE 2

| Ex. | Active ingredient | Concentration of active ingredient in the spray liquor in ppm | Efficacy in % of the untreated control |
|---|---|---|---|
| 1 V | Control (untreated) | (100% infection) | 0 |
| 2 V | Compound I.32 from Tab. 1 | 0.5 | 60 |
|  |  | 0.25 | 50 |
| 3 V | II (= fosethyl-aluminum) | 5 | 0 |
|  |  | 2.5 | 0 |

TABLE 3

| Ex. | Mixtures according to the invention | Observed efficacy | Calculated efficacy*) |
|---|---|---|---|
| 4 | 0.5 ppm I.32 + 5 ppm II (mixture 1:10) | 90 | 60 |
| 5 | 0.25 ppm I.32 + 2.5 ppm II (mixture 1:10) | 80 | 50 |

*) calculated using Colby's formula

The test results show that the observed efficacy in all mixing ratios is higher than the efficacy which had been calculated beforehand using Colby's formula.

We claim:

1. A fungicidal composition, comprising synergistically effective amounts of a) a carbamate of formula I,

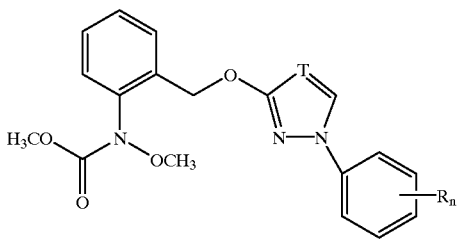

wherein T is CH or N, n is 0, 1 or 2 and R is halogen, $C_1$–$C_4$-alkyl or $C_1$–$C_4$-haloalkyl, wherein the radicals R are identical or different when n is 2, and b) an active compound of formula II,

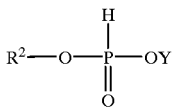

wherein

Y is hydrogen, a metal atom of the 1st to 3rd main group of the Periodic Table of the Elements or a group $NR^3R^4R^5R^6$;

$R^2$ is hydrogen, a $C_1$–$C_{18}$-alkyl group which is unsubstituted or substituted by halogen or a nitro group, a $C_2$–$C_8$-alkenyl or $C_2$–$C_8$-alkynyl group each of which is unsubstituted or substituted by halogen or a nitro group, a $C_1$–$C_8$-alkoxy-$C_1$–$C_8$-alkyl or a $C_2$–$C_8$-alkenyl-$C_1$–$C_8$-alkyl group, an unsubstituted or substituted aryl group having 6 to 14 carbons, a $C_3$–$C_7$-cycloalkyl group, a $C_1$–$C_4$-alkylaryl group or a heterocyclic group having 5 or 6 ring atoms and a hetero atom from the group consisting of N, O and S, where the heterocyclic group is attached directly or via an aliphatic chain to the oxygen atom, and $R^3$–$R^6$ independently of one another are each a $C_1$–$C_4$-alkyl group or a $C_1$–$C_4$-hydroxyalkyl group.

2. The fungicidal composition defined in claim 1, wherein Y is a metal of the 3rd main group.

3. The fungicidal composition defined in claim 2, wherein the metal of the 3rd main group is Al.

4. The fungicidal composition defined in claim 1, wherein $R^2$ is hydrogen or a $C_1$–$C_4$-alkyl group.

5. The fungicidal composition defined in claim 1, wherein Y is Al and $R^2$ is $CH_2$—$CH_3$.

6. A method for controlling harmful fungi, which comprises treating the harmful fungi, their habitat or plants, seeds, soils, areas, materials or spaces to be kept free from said fungi with synergistically effective amounts of the carbamate of formula I and the active compound of formula II defined in claim 1.

7. The method of claim 6, wherein from 0.005 to 0.5 kg/ha of the carbamate of formula I are applied.

8. The method of claim 6, wherein from 0.01 to 2 kg/ha of the active compound of formula II are applied.

* * * * *